United States Patent
Hayashi (10) Patent No.: US 6,409,344 B1
(45) Date of Patent: Jun. 25, 2002

(54) OCULAR REFRACTIVE-POWER MEASURING DEVICE

(75) Inventor: Takefumi Hayashi, Tokyo (JP)

(73) Assignee: Kabushiki Kaisha, Topcon, Tokyo (JP)

( * ) Notice: Subject to any disclaimer, the term of this patent is extended or adjusted under 35 U.S.C. 154(b) by 168 days.

(21) Appl. No.: 09/612,626

(22) Filed: Jul. 7, 2000

(30) Foreign Application Priority Data

Jul. 15, 1999 (JP) .......................... 11-201775

(51) Int. Cl.[7] .............................................. A61B 3/14
(52) U.S. Cl. ...................................................... 351/208
(58) Field of Search ............................... 351/205, 206, 351/208, 212, 221

(56) References Cited

U.S. PATENT DOCUMENTS 4,666,269 A * 5/1987 Nakamur et al. ............ 351/212
5,382,988 A * 1/1995 Nanjo ......................... 351/206
5,889,576 A    3/1999 Fujieda

FOREIGN PATENT DOCUMENTS

JP    11-19040    1/1999

* cited by examiner

Primary Examiner—George Manuel
(74) Attorney, Agent, or Firm—Burns, Doane, Swecker & Mathis, LLP (57) ABSTRACT

An ocular refractive-power measuring device includes: an alignment unit effecting alignment between a vertex of a cornea and a device body on the basis of corneal reflecting light; a refractive power measuring unit measuring the refractive power of an eye to be examined on the basis of the shape of a pattern light rays for ocular refractive power measurement reflected from a fundus of the eye to be examined; a storage unit storing the shape of the pattern light rays for ocular refractive power measurement; and an eclipse direction detecting system detecting the presence or absence of an eclipse in the pattern light rays due to a pupil of the eye to be examined on the basis of the shape of the pattern light rays stored in the storage unit, and detecting a direction of the eclipse. This alignment unit is arranged to effect adjustment of alignment between the pupil of the eye to be examined and the device body by adjustably moving the position of the device body on the basis of a result of detection by the eclipse direction detecting system.

6 Claims, 6 Drawing Sheets

OCULAR REFRACTIVE-POWER MEASURING DEVICE

BACKGROUND OF THE INVENTION

1. Field of the Invention

The present invention relates to an ocular refractive-power measuring device for calculating the refractive power of an eye to be examined by projecting light rays for measuring ocular refractive power toward the fundus of the eye to be examined and by analyzing the state of the reflected light.

2. Description of the Related Art

In an ocular refractive-power measuring device, the refractive power of an eye is measured by projecting the light rays of a pattern for measuring ocular refractive power through the pupil of an eye to be examined, and by receiving the light reflected from the fundus. Accordingly, if the optical axis of measurement and the center of the pupil are substantially offset from each other, the light rays of the pattern for measurement is eclipsed by the pupil, and a measurement error occurs. Hence, it is necessary to align the optical axis of measurement with the pupil at the time of measurement.

Meanwhile, an ophthalmologic apparatus, such as the ocular refractive-power measuring device and a non-contact type tonometer, is provided with an alignment detecting mechanism for optically detecting the position of the eye to be examined. As the detecting method, there have been proposed a method in which the optical axis of measurement is aligned with the corneal vertex by using the corneal reflecting light rays and a method in which the optical axis of measurement is aligned with the central position of the pupil by detecting an edge of the pupil on the basis of an image of the interior chamber.

In most eyes to be examined, the corneal vertex and the corneal center are generally aligned with each other, but there are not a few eyes to be examined in which the corneal vertex and the corneal center are offset from each other in cases where orthokeratologic operations or the like have been performed. For this reason, if the method of aligning the optical axis of measurement with the corneal vertex by using the corneal reflecting light rays is adopted in the ocular refractive-power measuring device, even if the completion of alignment is detected, there can be cases in which the pupil is actually eccentric with the optical axis of measurement. Consequently, the light rays of the chart for measuring ocular refractive power is eclipsed by the pupil, resulting in a measurement error.

To solve this problem, in Japanese Patent Unexamined Publication No. Hei.11-19040, alignment detection is effected by the corneal reflecting light rays, and the position of the pupil is also detected after detection of the completion of alignment. If it is determined that the pupil is offset, an automatic alignment mechanism is driven (if the automatic alignment is not adopted, an alignment inducing mark is displayed on a monitor so as to prompt an examiner to effect manual alignment) so as to align the optical axis of measurement with the pupil, thereby preventing an increase in the measurement error or the occurrence of the measurement error itself.

With Japanese Patent Unexamined Publication No. Hei.11-19040, however, a control mechanism for effecting automatic alignment based on a pupillary image is present in conjunction with a control mechanism for effecting automatic alignment based on the corneal reflecting light, and after detection of the alignment based on the corneal reflecting light, the position of the pupil is detected and whether or not the pupil is within a predetermined range is detected. If this method is adopted, after completion of the automatic alignment based on the corneal reflecting light, an additional time period longer than 1/30 second is further required for detection of the position of the pupil. In the meantime, despite the fact that the alignment with the corneal vertex has been successfully completed, there is a possibility of the eye to be examined becoming positionally offset again due to involuntary eye movement or the like, thereby making it difficult to complete the alignment.

SUMMARY OF THE INVENTION

Accordingly, an object of the invention is to provide an ocular refractive-power measuring device which has a mechanism for alignment with the corneal vertex for facilitating the detection of a signal, and which is capable of reducing an error in the measurement of the ocular refractive power as much as possible.

To attain the above object, there is provided an ocular refractive-power measuring device for measuring the refractive power of an eye to be examined, comprising: a refractive power measuring unit projecting pattern light rays for refractive power measurement onto a fundus of the eye to be examined, receiving the reflected light of the pattern light rays from the fundus by a light receiving element and measuring the refractive power of the eye to be examined on the basis of a shape of the pattern light rays projected onto said light receiving element; an alignment detecting unit projecting light rays for alignment detection toward the eye to be examined and detecting a state of alignment between a vertex of a cornea of the eye to be examined and a device body on the basis of corneal reflecting light of the light rays for alignment detection; an alignment unit aligning the device body on the basis of an output of the alignment detecting unit; a storage unit storing the shape of the pattern light rays received by the light receiving element; and an eclipse detecting unit detecting the presence of an eclipse in the pattern light rays due to a pupil of the eye to be examined on the basis of the shape of the pattern light rays stored in the storage unit, and a direction of the eclipse, wherein, when the eclipse detecting unit detects that the eclipse is present, the alignment unit adjust moves a position of the device body on the basis of a result of detection by the eclipse detecting unit such as to adjust an alignment between the pupil of the eye to be examined and the device body.

In accordance with the ocular refractive-power measuring device, alignment with a corneal vertex is effected by the alignment unit, and the pattern light rays for ocular refractive power measurement is projected toward the fundus of the eye to be examined. The pattern light rays reflected from the fundus is received by the light receiving element, and the refractive power of the eye to be examined is measured on the basis of the shape of the pattern light rays.

The pattern light rays received by the light receiving element is stored by the storage unit, and the eclipse direction detecting system detects the presence or absence of an eclipse in the pattern light rays due to the pupil of the eye to be examined on the basis of the shape of the pattern light rays stored in the storage unit, and detects the direction of the eclipse if the eclipse is present.

If it is determined by the eclipse direction detecting system that an eclipse is present, adjustment of alignment between the pupil of the eye to be examined and the device body is effected by adjustably moving the position of the device body on the basis of the result of detection by the eclipse direction detecting system.

In a case where a positional offset is present between the corneal center and the pupillary center, adjustment of alignment between the pupil of the eye to be examined and the device body can be effected on the basis of the result of detection by the eclipse direction detecting system. Therefore, the eclipse of the pattern light rays by the pupil can be eliminated, so that an error in the measurement of refractive power can be reduced.

In addition, in a case where there is no positional offset between the corneal center and the pupillary center, the refractive power can be measured on the basis of the pattern light rays stored by the storage unit, so that the possibility of the eye to be examined becoming positionally offset due to involuntary eye movement or the like can be reduced.

In addition, the alignment adjustment based on the result of detection by the eclipse direction detecting system may be effected manually. However, if movement controlling unit is provided for controlling the movement of the position of the device body on the basis of the result of detection by the eclipse direction detecting system, it is possible to effect the alignment adjustment by automatic control. In this case, as a mechanism for driving the position of the device body, a driving mechanism for effecting the adjustment of alignment with the corneal vertex can be made to serve a double purpose.

DETAILED DESCRIPTION OF THE PREFERRED EMBODIMENTS

Referring now to the drawings, a description will be given of an embodiment of the invention.

Figure 1:
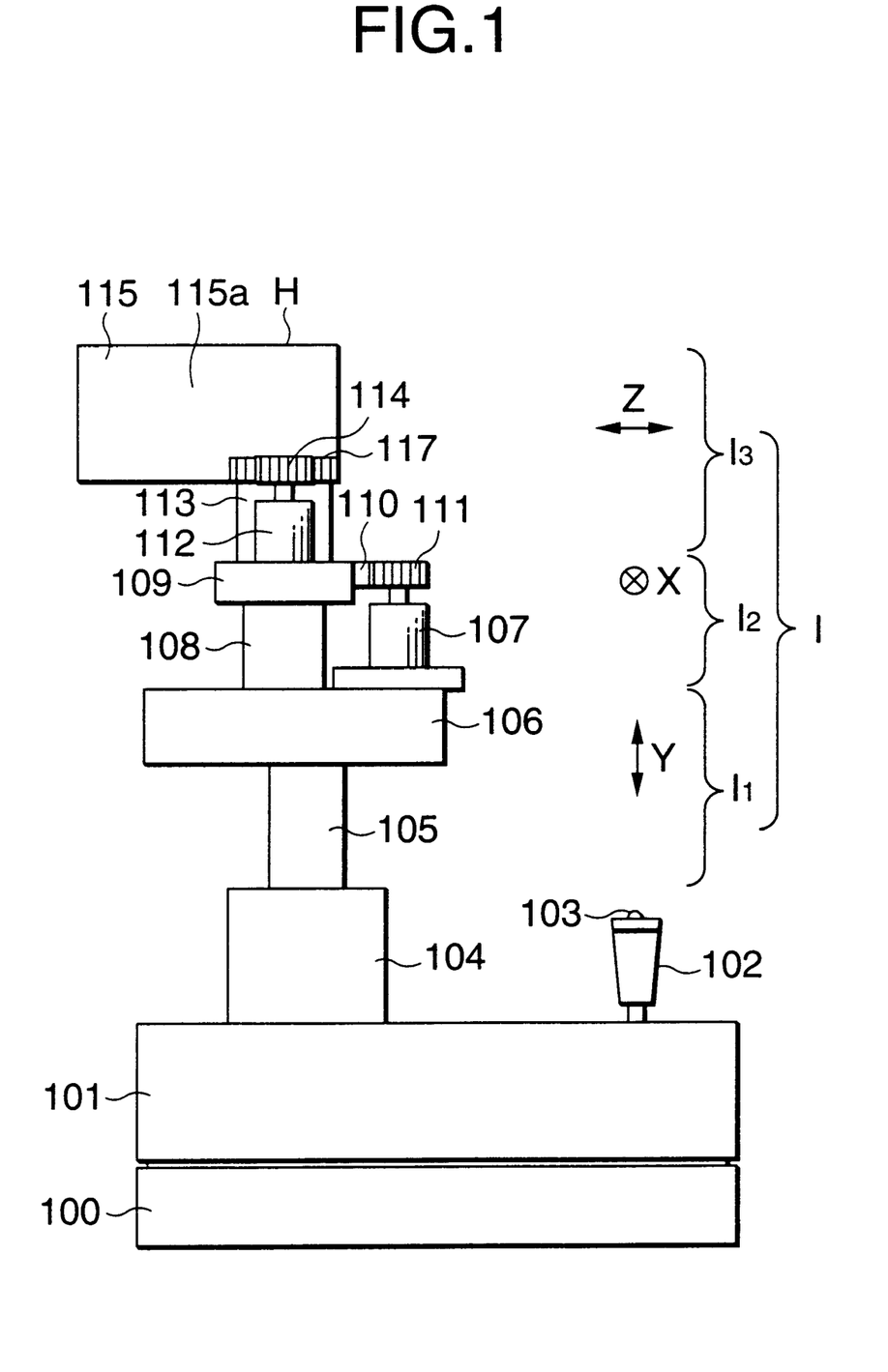
FIG. 1 is a schematic diagram explaining an alignment mechanism of an ocular refractive-power measuring device in accordance with an embodiment.

As shown in FIG. 1, in an ocular refractive-power measuring device in accordance with an embodiment of the invention, a mount 101 is disposed on a base 100 in such a manner as to be movable in the left-and-right direction (hereafter referred to as the x direction) and in the back-and-forth direction (hereafter referred to as the z direction). As a result, a device body H (which will be described later) is adjustably movable in the left-and-right direction and back-and-forth direction. Further, a joystick 102 for adjusting the position of the mount 101 is provided on the mount 101.

An alignment mechanism (alignment unit) I is comprised of a lifting mechanism I1 for adjustably moving a main body case 115 in the vertical direction (hereafter referred to as the y direction), a traversing mechanism I2 for adjustably moving the main body case 115 in the x direction, and a back-and-forth moving mechanism I3 for adjustably moving the main body case 115 in the z direction.

The lifting mechanism I1 includes a motor 104 such as a stepping motor fixed on top of the mount 101, a column 105 held in such a manner as to capable of being raised or lowered in the y direction relative to the mount 101 on the basis of the driving of the motor 104, and a table 106 fixed to an upper end of the column 105. As the motor 104 is rotated, the table 106 is raised or lowered in the y direction.

The traversing mechanism I2 has a motor 107, such as a stepping motor, and a column 108 which are fixed on the table 106, as well as a table 109 which is held on an upper end of the column 108 in such a manner as to be movable in the x direction. Further, a rack 110 is attached to a side surface of the table 109, while a pinion 111 is attached to an output shaft of the motor 107. The rack 110 and the pinion 111 mesh with each other. As a result, as the motor 107 is rotated, the table 109 is slidably moved in the x direction relative to the column 108.

The back-and-forth moving mechanism I3 has a motor 112, such as a stepping motor, and a column 113 which are fixed on the table 109, a pinion 114 provided on an output shaft of the motor 112, and a main body case 115 disposed on the column 113 in such a manner as to be slidable in the z direction. A rack 117 is attached to a side surface 115a of the case 115, and the rack 117 meshes with the pinion 114. As a result, as the motor 112 is rotated, the case 115 is slidably moved in the z direction relative to the column 113.

Figure 2:
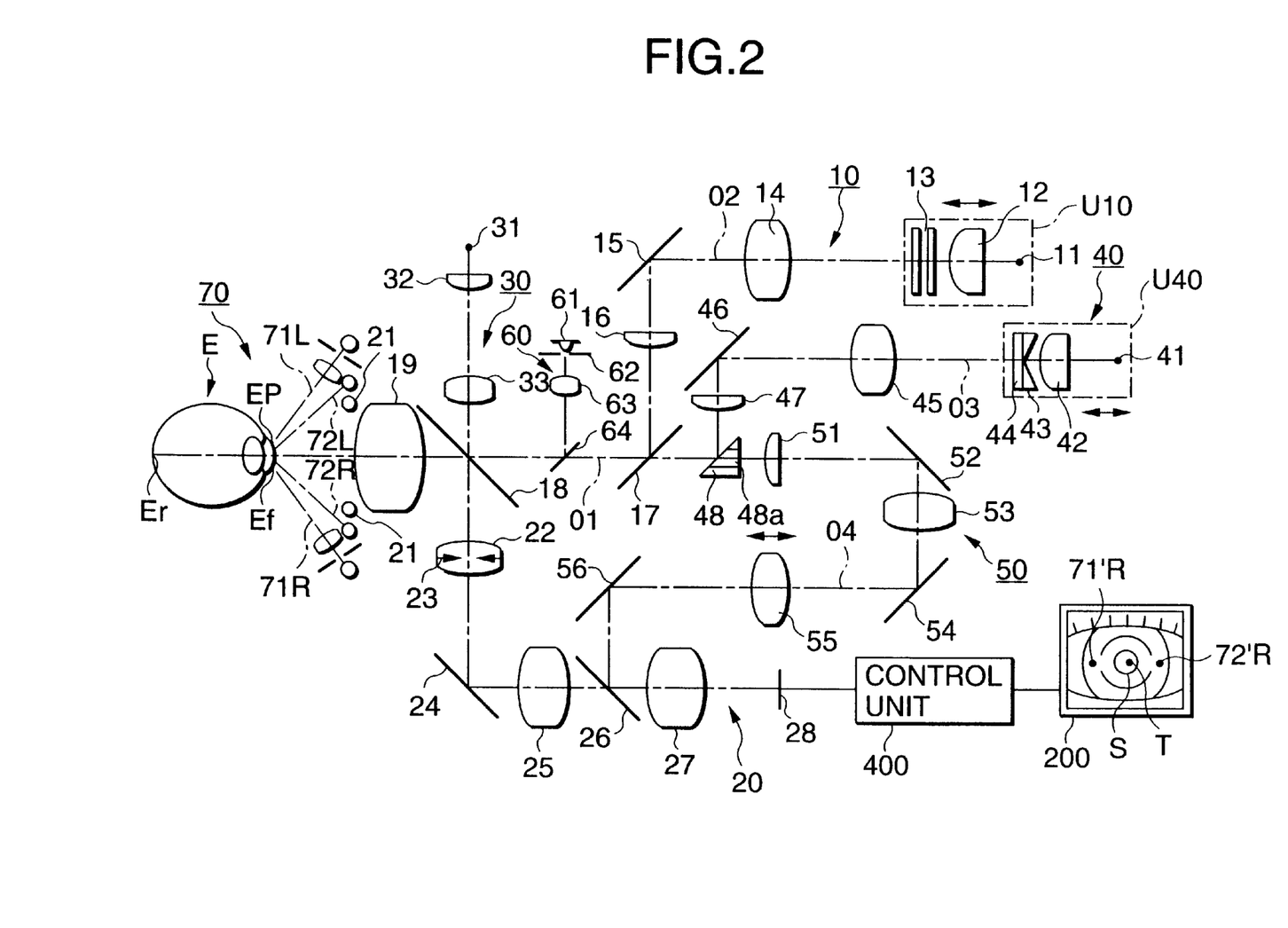
FIG. 2 is an explanatory diagram illustrating schematic configurations of optical systems and a control unit of the ocular refractive-power measuring device in accordance with the embodiment.

As shown in FIG. 2, a signal processing and computing unit (control unit) 400, which is specified in the invention of this application and includes a known control system, is accommodated in the main body case 115.

In FIG. 2, reference numeral 10 denotes a fixation chart projecting optical system for projecting a fixation chart onto the fundus Er to fixate and fog an eye E to be examined. Numeral 20 denotes an observing optical system for observing the anterior chamber Ef of the eye E to be examined. Numeral 30 denotes a scale projecting optical system for projecting a sighting scale S onto a CCD 28 serving as a light receiving element. Numeral 40 denotes a pattern light rays projecting optical system for projecting a pattern light rays onto the fundus Er for measuring the refractive power of the eye E to be examined. Numeral 50 denotes a light receiving optical system for allowing the light rays reflected from the fundus Er to be received by the CCD 28 serving as the light receiving element. Numeral 60 denotes an alignment light projecting system for projecting chart light onto the eye E to be examined for detecting a state of alignment in a direction perpendicular to the optical axis (an amount of offset Δxy in the x and y directions). Numeral 70 denotes an operating distance detecting system for detecting an operating distance between the eye E to be examined and the device body H (an amount of offset Δz in the z direction). Numeral 200 denotes a TV monitor serving as a display unit.

In addition, reference numeral 400 denotes the signal processing and computing unit (control unit) which includes: a known system for automatically controlling the alignment in the x, y, and z directions; a computing unit for computing the refractive power of the eye E to be examined on the basis of the shape of the pattern light rays reflected from the fundus Er; unit for inputting and outputting other necessary information; and various controlling unit.

The fixation chart projecting optical system 10 includes a light source 11, a collimator lens 12, a chart plate 13, a relay lens 14, a mirror 15, a relay lens 16, a dichroic mirror 17, a dichroic mirror 18, and an objective lens 19.

The visible light emitted from the light source 11 is converted to parallel light rays by the collimator lens 12, and is then transmitted through the chart plate 13. The chart plate 13 is provided with a target for fixating and fogging the eye E to be examined. The target light rays are transmitted through the relay lens 14 and are reflected by the mirror 15. This reflected light is transmitted through the relay lens 16 and is then reflected by the dichroic mirror 17. The reflected light, after being guided to a principal optical axis O1 of the device body H, is transmitted through the dichroic mirror 18, and is passed through the objective lens 19 so as to be guided to the eye E to be examined.

It should be noted that the light source 11, the collimator lens 12, and the chart plate 13 are integrally formed as a fixation chart projecting unit U10. This fixation chart projecting unit U10 is arranged to be movable along an optical axis O2 of the fixation chart projecting optical system 10 so as to fixate and fog the eye E to be examined. The fixation chart for fixating and fogging is projected onto the eye E to be examined by the fixation chart projecting optical system 10.

The observing optical system 20 includes a light source 21, the objective lens 19, the dichroic mirror 18, a relay lens 22, a diaphragm 23, a mirror 24, a relay lens 25, a dichroic mirror 26, an image forming lens 27, and the CCD 28.

The light rays emitted from the light source 21 are directly applied to the anterior chamber Ef of the eye E to be examined. The light rays reflected by the anterior chamber Ef are passed through the objective lens 19 and are then reflected by the dichroic mirror 18. The reflected light rays pass through the diaphragm 23 at the same time as they are transmitted through the relay lens 22. Subsequently, after being reflected by the mirror 24, the light rays are transmitted through the relay lens 25 and the dichroic mirror 26, and reach the CCD 28 through the image forming lens 27, thereby forming an image of the anterior chamber on the imaging surface of the CCD 28. This anterior chamber image is displayed on the screen of the monitor 200 through the control unit 400, so that the examiner is able to observe the anterior chamber image through the observing optical system 20.

The scale projecting optical system 30 includes a light source 31, a collimator lens 32 provided with a sighting scale, a relay lens 33, the dichroic mirror 18, the relay lens 22, the diaphragm 23, the mirror 24, the relay lens 25, the dichroic mirror 26, and the image forming lens 27.

The light rays emitted from the light source 31 are converted to parallel light rays when they are transmitted through the collimator lens 32. Subsequently, the light rays pass through the relay lens 33, the dichroic mirror 18, the relay lens 22, and the diaphragm 23, and are then reflected by the mirror 24. The light rays further pass through the relay lens 25 and the dichroic mirror 26, thereby forming an image on the CCD 28 by the image forming lens 27.

The video signal from the CCD 28 is outputted to the monitor screen through the control unit 400, and an annular scale image S is displayed on the monitor screen together with the anterior chamber image guided by the observing optical system 20.

The pattern light rays projecting optical system 40 includes: a light source 41; a collimator lens 42; a conical prism 43; a ring chart plate 44; a relay lens 45; a mirror 46; a relay lens 47 with an annular aperture 47' formed therein; a bored prism 48; the dichroic mirror 17, the dichroic mirror 18, and the objective lens 19. It should be noted that the light source 41 and the annular opening 47' are optically conjugative, and the annular aperture 47' and a pupil EP of the eye E to be examined are located at optically conjugative positions.

It should be noted that the light source 41, the collimator lens 42, the conical prism 43, and the ring chart plate 44 are formed integrally as a pattern light rays projecting unit U40, and are movable along an optical axis O3 of the pattern light rays projecting optical system 40.

The light rays emitted from the light source 41 are converted to parallel light rays by the collimator lens 42, are then transmitted through the conical prism 43. Subsequently, the light rays are guided to the ring chart plate 44 and are transmitted through a ring-shaped pattern portion formed in the ring chart plate 44 so as to be converted to pattern light rays. The pattern light rays, after being transmitted through the relay lens 45, is reflected by the mirror 46, is transmitted through the relay lens 47, and is reflected along the principal optical axis O1 by the bored prism 48. Subsequently, after being transmitted through the dichroic mirrors 17 and 18, the pattern light rays form an image on the fundus Er by the objective lens 19. The pattern light rays for measuring the refractive power of the eye E to be examined can be projected onto the fundus Er by this pattern light rays projecting optical system 40.

The light receiving optical system 50 includes: the objective lens 19; the dichroic mirrors 18 and 17; a bored portion 48a of the bored prism 48; a relay lens 51; a mirror 52; a relay lens 53; a mirror 54; a focusing lens 55; a mirror 56; the dichroic mirror 26, the image forming lens 27, and the CCD 28.

It should be noted that the focusing lens 55 is movable along an optical axis O4 of the light receiving optical system 50 in interlocking relation to the movement of the pattern light rays projecting unit U40.

The reflected light rays, which have been guided to the fundus Er by the pattern light rays projecting optical system 40 and reflected by the fundus Er, are focused by the objective lens 19, are transmitted through the dichroic mirrors 18 and 17, are guided to the bored portion 48a of the bored prism 48, and pass through the bored portion 48a.

The pattern reflected light rays which passed through the bored portion 48a are transmitted through the relay lens 51, are reflected by the mirror 52, are transmitted through the relay lens 53, are reflected by the mirror 54, are transmitted through the focusing lens 55, are reflected by the mirror 56 and the dichroic mirror 26, reaches the CCD 28 by the image forming lens 27, thereby forming an annular pattern image on the CCD 28. On the basis of the annular pattern image, the presence or absence of an eclipse of the pattern light rays due to the pupil in accordance with the invention, as well as its range, are measured by an eclipse direction detecting system, and the refractive power of the eye E to be examined is computed by the control unit 400.

The alignment light projecting system 60 has an LED 61, a pinhole 62, a collimator lens 63, and a half mirror 64, and has the function of projecting an alignment chart light rays onto the cornea. The alignment chart light rays projected toward the eye E to be examined as parallel light rays are reflected by the cornea of the eye E to be examined, and an alignment chart image T is projected onto the CCD 28 by the light receiving optical system 50. When this alignment chart image T reaches the vicinity of the center of the aforementioned sighting scale S, the fact that the alignment has been completed is detected.

The working distance detecting system 70 is for detecting the operating distance between the eye E to be examined and the device body H, and has two semi-arc infinite-distance charts projecting systems 71R and 71L for projecting charts from infinite distances and two finite-distance charts projecting systems 72R and 72L for projecting charts from finite distances, these two groups of projecting systems being arranged bilaterally symmetrically about the optical axis O1, respectively. Chart light rays from the four projecting systems are reflected by the cornea, and are projected onto the CCD 28 as chart images 71'R, 71'L, 72'R, and 72'L by the light receiving optical system 50. When these chart images have assumed a fixed positional relationship on the CCD 28, detection is made that the operating distance has become a distance Wo (not shown) suitable for measurement.

Figure 3:
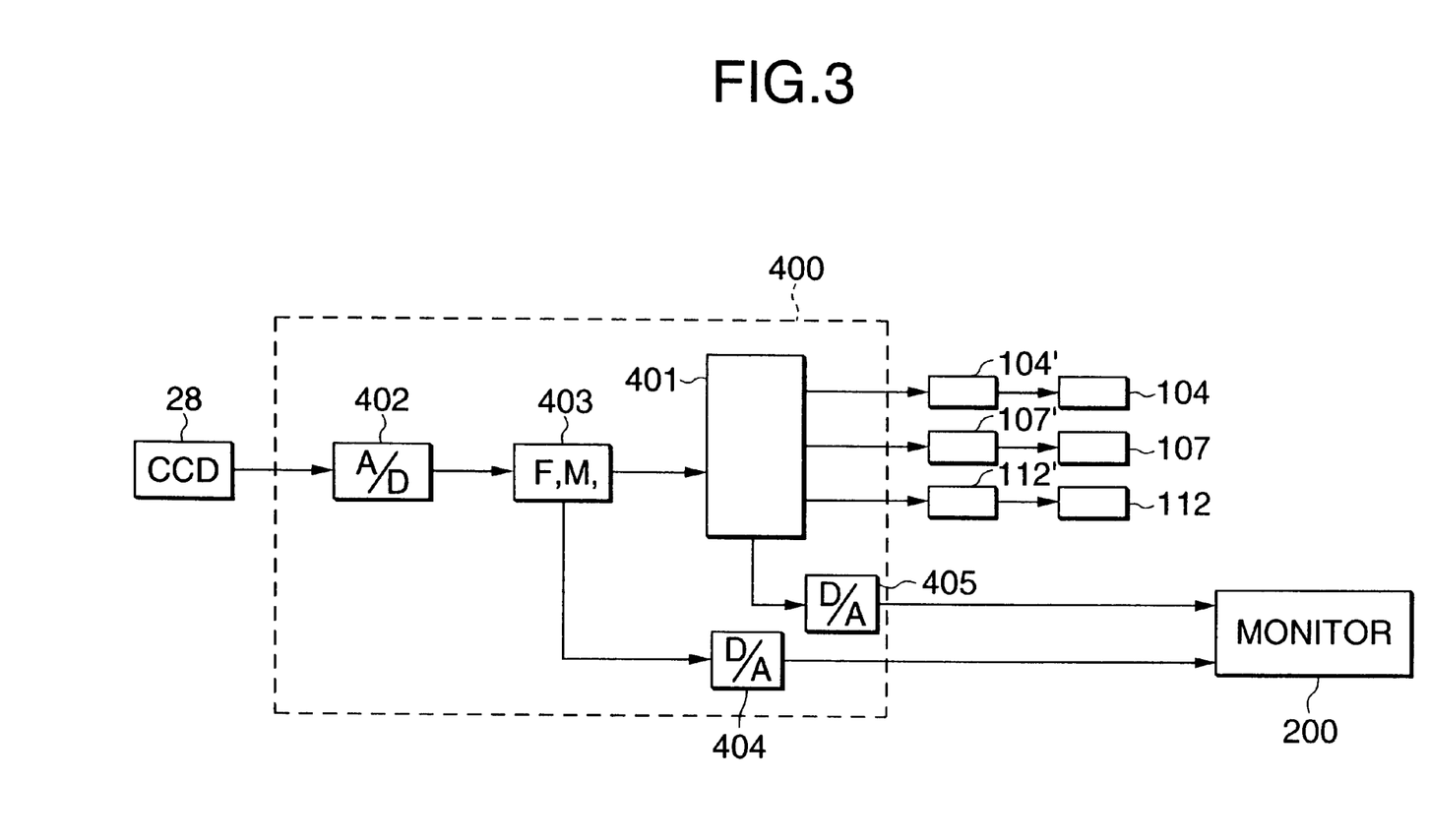
FIG. 3 is a block diagram illustrating a control unit 400 shown in FIG. 2.

As shown in FIG. 3, the control unit 400 includes a control circuit 401, an A/D converter 402, a frame memory 403, and D/A converters 404 and 405. The control circuit 401 is connected to the CCD 28 through the frame memory 403 and the A/D converter 402, and is connected to the motors 104, 107, and 112 of the above-described alignment mechanism I through drivers 104', 107', and 112', respectively. Further, the monitor 200 is connected to the frame memory 403 through the D/A converter 404, and is connected to the control circuit 401 through the D/A converter 405. Additionally, this frame memory 403 is controlled by the control circuit 401.

The control circuit 401 is connected to the joystick 102 and other input unit for inputting necessary information, output unit such as a printer, and control unit such as a driver for controlling the lighting of the various light sources, and includes an automatic alignment control system for automatically controlling alignment with the corneal vertex as well as a computing unit for computing the refractive power of the eye to be examined on the basis of the shape of the pattern light rays reflected by the fundus Er. For example, the control circuit 401 has the functions of effecting automatic alignment with the corneal vertex by transmitting and receiving information to and from the alignment mechanism I, and of computing the refractive power of the eye E to be examined on the basis of a pattern light rays image received by the light receiving element.

The control circuit 401 has the functions of computing the position of reception of the alignment chart image T received by the CCD 28 and of computing the amount of offset Δxy between the optical axis O1 and the corneal vertex of the eye E to be examined on the basis of the result of this computation. At the same time, the control circuit 401 outputs predetermined drive signals to the drivers 104' and 107' on the basis of the results of computation, thereby completing the automatic alignment in the x and y directions.

In addition, the control circuit 401 has the functions of computing the positions of reception of the chart images 71'R, 71'L, 72'R, and 72'L received by the CCD 28 and of computing the amount of offset Δz from the proper operating distance Wo on the basis of the results of this computation. At the same time, the control circuit 401 outputs a predetermined drive signal to the driver 112', thereby completing the automatic alignment in the z direction (adjustment of a proper operating distance).

Further, the control circuit 401 detects the presence or absence of an eclipse of the pattern light rays due to the pupil on the basis of the shape of the pattern light rays stored in the frame memory 403, and if the eclipse is present, the control circuit 401 detects its direction. On the basis of the result of this detection, drive signals are outputted to the drivers 104' and 107' to adjust the alignment between the pupil EP of the eye to be examined and the device body H.

Next, a description will be given of the method of detecting the direction of the eclipse.

Figure 4:
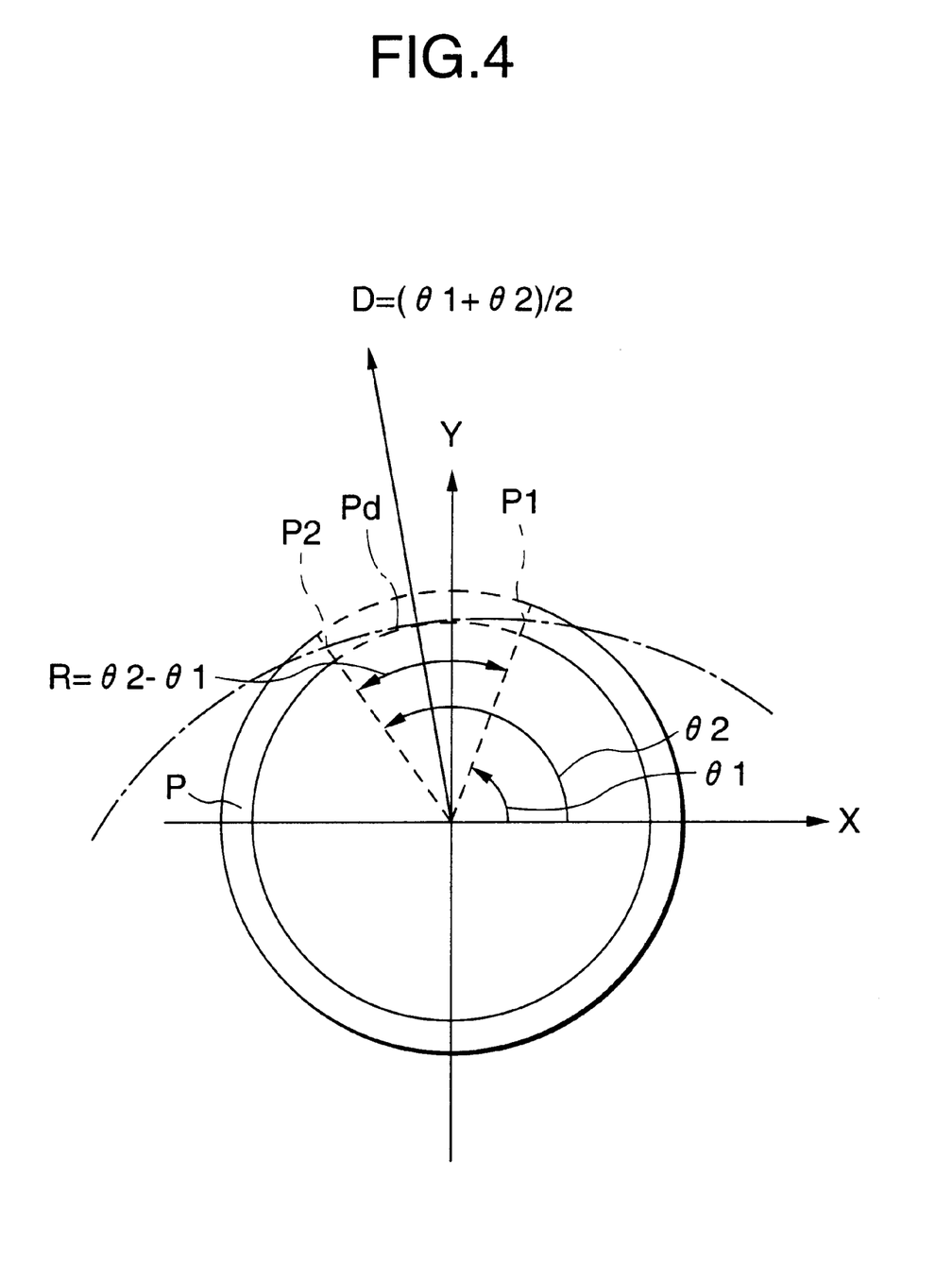
FIG. 4 is an explanatory diagram illustrating the state of an obscurity in a pattern light rays P subjected to binary processing in accordance with the embodiment.

FIG. 4 shows a case in which a portion of the annular pattern P between a position P1 and a position P2 has been obscured by an eclipse due to the pupil. Consideration will now be given to x-y orthogonal coordinates having the center O of the circular arc of a pattern image P as an origin. If it is assumed that the angle from the x axis as a reference to the position P1 is θ1 and that the angle from the x axis to the position P2 is θ2, the direction D of the obscurity in the pattern image P can be calculated as D=(θ1+θ2)/2 and that the range R of an obscurity Pd can be calculated as R=θ2−θ1. On the basis of the direction D of the obscurity and the range R of the obscurity, the direction in which the device body H is to be moved and the distance thereof are detected. On the basis of the results of this detection, the control circuit 401 transmits predetermined signals to the drivers 104' and 107'. Consequently, the device body H is moved in the direction in which the eclipse is eliminated, thereby completing the automatic alignment with respect to the pupillary center.

Next, a description will be given of the relationship between the direction D of the obscurity and the direction in which the device body H is to be moved.

Figure 6:
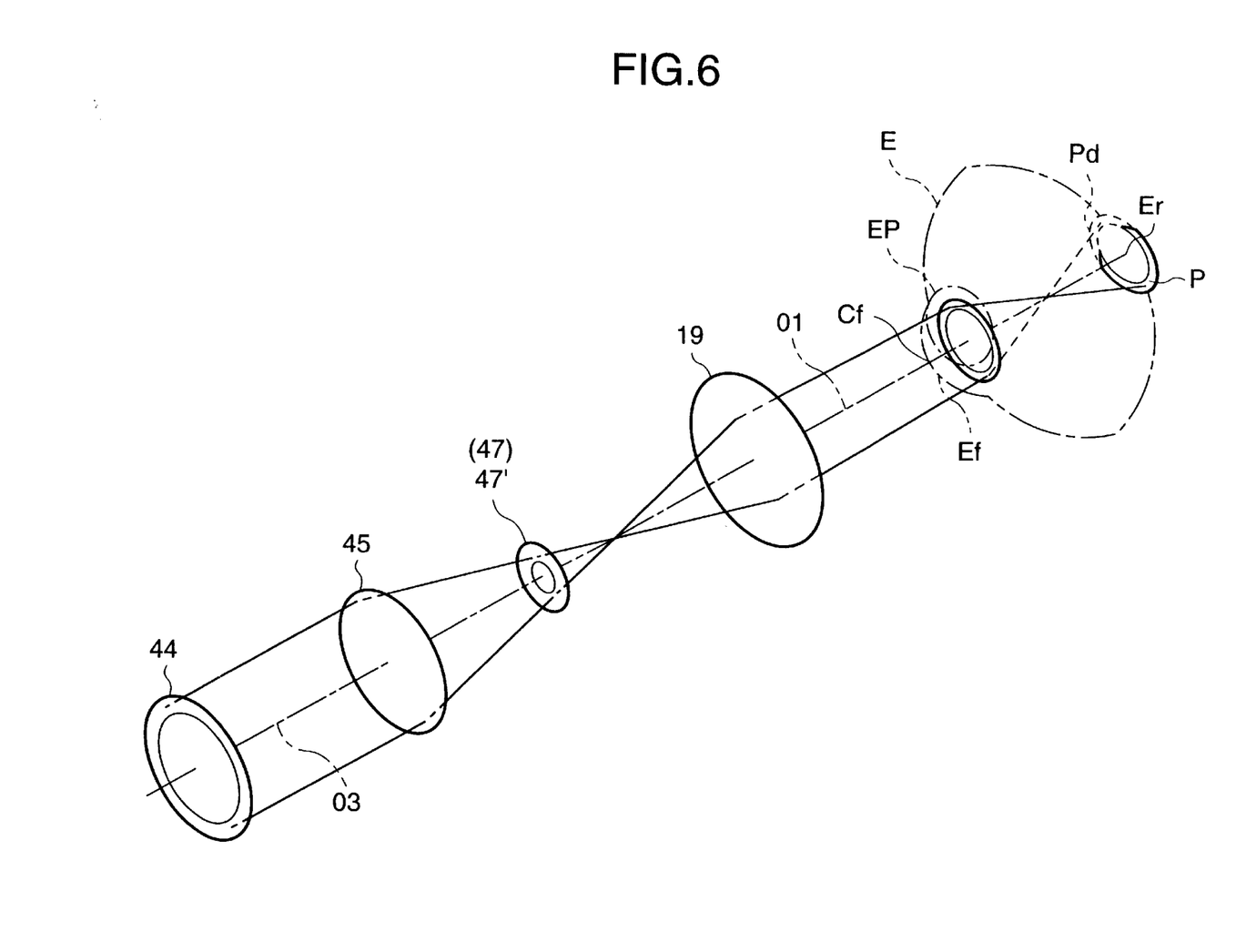
FIG. 6 is an explanatory diagram explaining the relationship of the direction of the obscurity on the pattern light rays P and the moving direction of a device body in accordance with the embodiment.

As described above, the annular aperture 47' of the pattern projecting optical system 40 is located in an optically conjugative position with the pupil EP of the eye E to be examined. Here, as shown in FIG. 6, it is assumed that a lower portion of the image of the annular aperture 47' formed in the vicinity of the pupil EP to be examined due to the projection of the ring pattern light rays from the pattern light rays projecting optical system 40 has been obscured by the eclipse by the pupil EP. Then, as for the image P of the ring pattern formed on the fundus Er, the upper side of the pattern image, contrary to the pupillary portion, is obscured due to the action of the crystalline lens to be examined. Namely, in a case where there is no astigmatism in the eye E to be examined, if the ring light rays in the pupil is eclipsed in a certain direction, the image of the ring pattern formed on the fundus Er becomes a ring image P having the obscurity Pd in a direction 180 degrees different from the direction of the eclipse.

Accordingly, in a case where the light receiving optical element 50 is arranged to observe an erect image, if the device body H is moved in the same direction of the direction D of the obscurity in the pattern image P, the obscurity Pd can be eliminated. In a case where the light receiving optical element 50 is conversely arranged to observe a reverse image, if the device body H is moved in the direction 180 degrees different from the direction D of the obscurity in the pattern image P, the obscurity Pd can be eliminated. In either case, the relationship between the direction D of the obscurity and the direction in which the device body H is to be moved can be different depending on the arrangement of the optical system.

Incidentally, in a case where astigmatism is present in the eye E to be examined, an arrangement may be provided such that the direction of moving the device body H is changed by taking the astigmatism degree into consideration.

The control of driving in the x and y directions may be performed automatically, but may be performed manually. In this case, it suffices if the data obtained by the eclipse direction detecting unit is displayed on the monitor screen, and the examiner is prompted to effect alignment adjustment.

Figure 5:
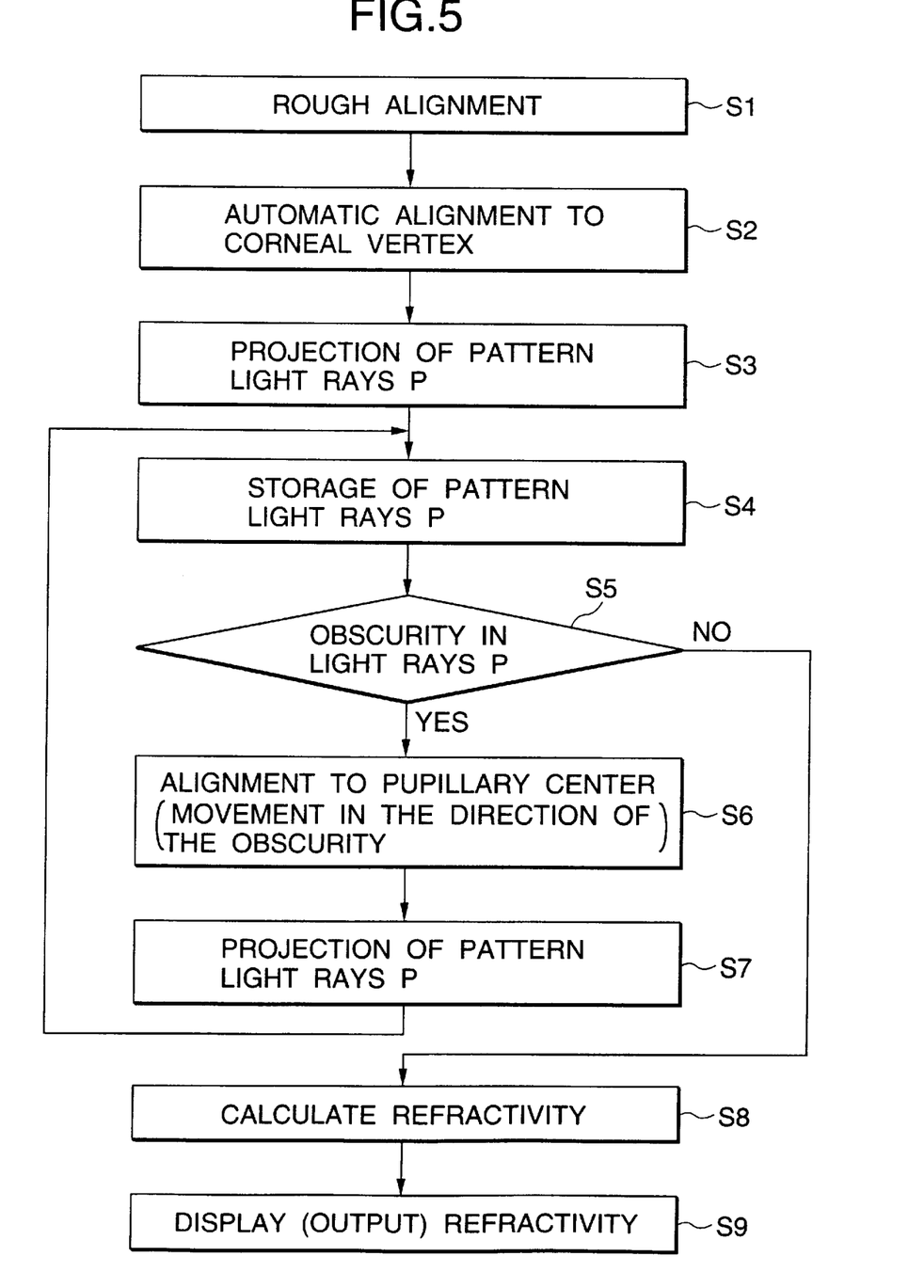
FIG. 5 is a flowchart explaining the operation of the ocular refractive-power measuring device in accordance with the embodiment.

Next, referring to FIG. 5, a description will be given of the operation of this refractive power measuring device.

The examiner lights up the respective light sources of the observing optical system 20, the scale projecting optical system 30, the alignment light projecting system 60, and the operating distance detecting system 70, and effects rough alignment by operating the joystick 102 serving as an operating member on the basis of the anterior chamber image being displayed on the monitor screen, such that the pupil EP to be examined is brought to the vicinity of the center of the screen (Step S1).

Upon completion of the rough alignment, the alignment chart image T and the chart images 71'R, 71'L, 72'R, and 72'L appear on the monitor screen. Subsequently, alignment detection based on the alignment light projecting system 60 and the operating distance detecting system 70 is started, whereupon the alignment mechanism I starts operation, thereby starting the automatic adjustment of alignment with a corneal vertex Cf (Step S2).

When completion of the automatic adjustment of alignment with a corneal vertex Cf is thus detected, the processing unit 400 causes the light source 41 for measurement of ocular refractive power to emit light by a projection controlling unit. Consequently, a pattern light rays P for measurement of ocular refractive power is projected onto the fundus Er, thereby forming a pattern image P on the CCD 28 (Step S3). The CCD 28 effects photoelectric conversion of the image and outputs a video signal. The video signal is inputted to the A/D converter 402, and after conversion from an analog signal to a digital signal by the A/D converter 402, the video signal is temporarily stored in the frame memory 403 (Step S4).

On the basis of the image data stored in the frame memory 403, the control circuit 401 subjects the pattern image P to binary processing. Then, a determination is made by the eclipse direction detecting unit as to whether or not an obscurity is present in the pattern image P thus extracted. If it is determined that an obscurity is present in the pattern image P, the direction D of the obscurity and its range R are calculated (Step S5).

If it is determined in Step 5S that an obscurity is not present (N), an eclipse due to the pupil EP is absent, the operation proceeds to Step S8 to calculate the refractive power by a known refractive power calculating unit on the basis of the pattern light rays P projected in Step S3. In Step S9, the refractive power is printed out by the printer, and the refractive power is displayed on the monitor screen.

Further, if it is determined in Step S5 that an obscurity is present (Y) in the pattern image P, the operation proceeds to Step S6. In Step S6, on the basis of the results of calculation of the direction D of the obscurity in the pattern light rays image P and its range R, the control circuit 401 outputs predetermined drive signals to the drivers 104' and 107' to drive the device body in the direction in which the eclipse due to the pupil is eliminated, thereby adjusting the alignment with the pupillary center.

Next, upon detection of the completion of the alignment adjustment, the operation proceeds to Step S7, in which the control circuit 401 causes the light source 41 to emit light again by the projection controlling unit. Consequently, the pattern light rays P for measurement of ocular refractive power is projected again onto the fundus Er, thereby forming the pattern image P on the CCD 28. The CCD 28 effects photoelectric conversion of the image and outputs a video signal. The video signal is inputted to the A/D converter 402, and after conversion to a digital signal by the A/D converter 402, the video signal is temporarily stored in the frame memory 403 (Step S4).

Next, the operation proceeds to Step 5S in which the control circuit 401 subjects the pattern image P to binary processing again on the basis of the image data newly stored in the frame memory 403. Then, a determination is made by the eclipse direction detecting unit as to whether or not an obscurity is present in the pattern image P thus extracted. If it is determined that an obscurity is present in the pattern image P, the direction D of the obscurity and its range R are calculated (Step S5). Since this pattern image P has been subjected to the adjustment of alignment with the pupillary center in Step S6, the pattern image P is generally free from the eclipse due to the pupil.

If this obscurity is absent (N), the operation proceeds to Step S8, in which the refractive power is calculated on the basis of the shape of the pattern light rays stored in Step S4. The refractive power is then outputted in Step S9.

As described above, a detailed description has been given of the embodiment of the invention with reference to the drawings, but a specific arrangement is not limited to this embodiment, and various modifications of design and the like are included in the invention insofar as they do not depart from the gist of the invention.

For example, as for the storage into the frame memory when the operation has proceeded from Step S7 to S4, an arrangement may be provided such that outdated information being stored is updated and the updated information is stored.

In addition, depending on the state of the eye to be examined, there are cases where the eclipse of the pattern light rays cannot be eliminated even if the alignment adjustment is performed a predetermined number of times. In that case, an appropriate terminating operation may be incorporated such as by displaying an error and suspending the projection of the pattern light rays.

Since the arrangement is provided as described above, it is possible to provide an ocular refractive-power measuring device which has a mechanism for alignment with the corneal vertex for facilitating the detection of a signal, and which is capable of reducing an error in the measurement of the ocular refractive power as much as possible.

What is claimed is:

1. An ocular refractive-power measuring device for measuring the refractive power of an eye to be examined, comprising:

a refractive power measuring unit projecting pattern light rays for refractive power measurement onto a fundus of the eye to be examined, receiving the reflected light of the pattern light rays from the fundus by a light receiving element and measuring the refractive power of the eye to be examined on the basis of a shape of the pattern light rays projected onto said light receiving element;

an alignment detecting unit projecting light rays for alignment detection toward the eye to be examined and detecting a state of alignment between a vertex of a cornea of the eye to be examined and a device body on the basis of corneal reflecting light of the light rays for alignment detection;

an alignment unit aligning said device body on the basis of an output of said alignment detecting unit;

a storage unit storing the shape of the pattern light rays received by said light receiving element; and an eclipse detecting unit detecting the presence of an eclipse in the pattern light rays due to a pupil of the eye to be examined on the basis of the shape of the pattern light rays stored in said storage unit, and a direction of the eclipse, wherein, when said eclipse detecting unit determines that the eclipse is present, said alignment unit moves a position of said device body on the basis of a result of detection by said eclipse detecting unit such as to adjust an alignment between the pupil of the eye to be examined and said device body.

2. The ocular refractive-power measuring device according to claim 1, further comprising:

a movement controlling unit controlling the movement of the position of said device body on the basis of the result of detection by said eclipse detecting unit.

3. The ocular refractive-power measuring device according to claim 1, wherein said eclipse detecting unit detects a dimension of the eclipse, and said alignment unit adjustably moves the position of said device body on the basis of the direction and the dimension of the eclipse detected by said eclipse detecting unit.

4. The ocular refractive-power measuring device according to claim 1, further comprising:

an operating distance detecting unit detecting an operating distance between the eye to be examined and said device body, wherein said alignment unit aligns said device body on the basis of an output of said operating distance detecting unit.

5. An ocular refractive-power measuring method for measuring the refractive power of an eye to be examined, comprising the steps of:

aligning a device body to a corneal vertex of the eye to be examined;

projecting pattern light rays for refractive power measurement onto a fundus of the eye to be examined;

receiving the reflected light of the pattern light rays from the fundus by a light receiving element;

storing a shape of the pattern light rays received by said light receiving element;

detecting a presence of an eclipse of the pattern light rays due to a pupil of the eye to be examined on the basis of the shape of the pattern light rays; and adjusting an alignment between the pupil of the eye to be examined and said device body by moving a position of said device body on the basis of the result of detection by said eclipse detecting step, when detecting that the eclipse is present in said eclipse detecting step.

6. The ocular refractive-power measuring method according to claim 5, wherein said eclipse detecting step further detects a direction and a dimension of the eclipse when the eclipse is present, wherein said adjusting step moves the position of said device body on the basis of the direction and the dimension of the eclipse.

* * * * *